United States Patent [19] [11] Patent Number: 4,601,703
Herlitze [45] Date of Patent: Jul. 22, 1986

| [54] | INJECTOR FOR AN INFUSION OR TRANSFUSION SYSTEM |
|---|---|
| [75] | Inventor: Gerhard Herlitze, Baunatal, Fed. Rep. of Germany |
| [73] | Assignee: Intermedicat GmbH, Emmenbrucke, Switzerland |
| [21] | Appl. No.: 683,865 |
| [22] | Filed: Dec. 20, 1984 |
| [30] | Foreign Application Priority Data |
| | Jan. 27, 1984 [DE] Fed. Rep. of Germany ... 8402311[U] |
| [51] | Int. Cl.$^4$ ................................................ A61M 5/00 |
| [52] | U.S. Cl. ........................................ 604/86; 604/415 |
| [58] | Field of Search ................ 604/86, 88, 201–206, 604/905, 411–414 |

[56] References Cited

U.S. PATENT DOCUMENTS

| 3,682,315 | 8/1972 | Haller | 604/415 |
| 3,900,028 | 8/1975 | McPhee | 604/415 |
| 4,187,149 | 2/1980 | Tolbert et al. | 604/415 |
| 4,219,912 | 9/1980 | Adams | 604/86 |
| 4,289,129 | 9/1981 | Turner | 604/86 |
| 4,307,766 | 12/1981 | Tanokura | 604/415 |

Primary Examiner—C. Fred Rosenbaum
Assistant Examiner—Karen L. Kaechele
Attorney, Agent, or Firm—Kenyon and Kenyon

[57] ABSTRACT

An injector for infusion or transfusion systems utilizes a housing having a duct extending longitudinally therethrough. The inner surface of a penetrable membrane covers an end of the duct, with the edge of the surface abutting an annular shoulder of the housing. A ring is disposed in an annular indentation on the periphery of the outer surface of the membrane, with the outer edge of the inner surface of the ring abutting a second annular shoulder of the housing. The outer surface of the ring and the central portion of the outer surface of the membrane are flush.

6 Claims, 1 Drawing Figure

U.S. Patent   Jul. 22, 1986   4,601,703
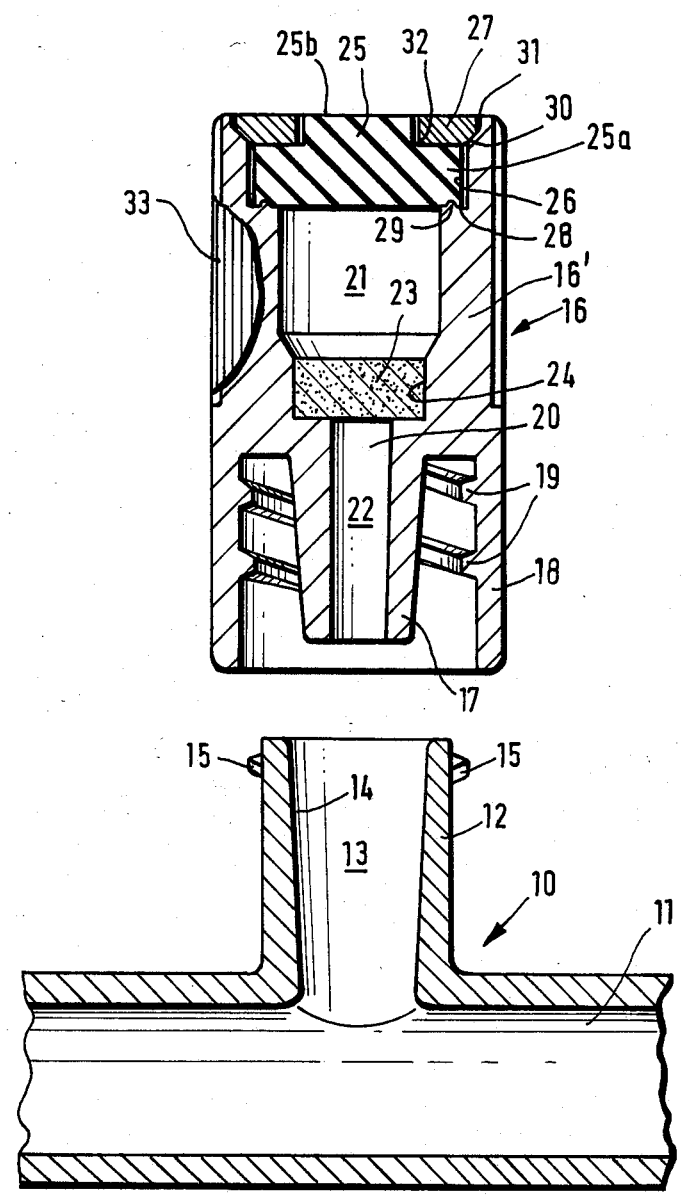

INJECTOR FOR AN INFUSION OR TRANSFUSION SYSTEM

BACKGROUND OF THE INVENTION

1. Field of the Invention

The present invention relates generally to infusion or transfusion systems, and more particularly to an injector utilized therein.

2. Description of the Prior Art

The injector disclosed in U.S. Ser. No. 550,086, filed Nov. 9, 1983, assigned to the present assignee, comprises a cylindrical housing containing a duct. The outlet of the duct is configured for insertion into a nipple on a transfer tube. The inlet of the duct is covered by a membrane. The membrane can be penetrated by a cannula of a syringe in order to injecet a substance into the duct of the housing. A thick, porous material is disposed within the duct between the outlet and the inlet, to filter out solid particles that may contaminate the injected substance. The end of the housing proximate the membrane extends over the membrane, forming a cap which securely positions the membrane against the inlet of the duct. A hole is disposed in the cap through which a cannula may be inserted into the membrane. The edge of the cap surrounding the hole is turned inward, toward the membrane, pressing the membrane against a shoulder of the housing proximate the inlet of the duct. Owing to the elasticity of the membrane, its central portion protrudes somewhat, forming a convex surface covering the inside of the hole. Accordingly, a recess is created where the periphery of this convex surface meets the edge of the cap bounding the hole.

Disinfection of the membrane around a cannula puncture point is difficult, since germs may invade the recess, where they settle and are substantially protected from sterilization. Also, moisture may accumulate in the recess, affording a fostering culture medium or such germs. The puncture region of the membrane, being arched, jeopardizes disinfection.

Thus, there is a need for an injector having a membrane whose puncture zone is easy to keep clean and to disinfect.

SUMMARY OF THE INVENTION

The present invention entails an injector for infusion or transfusion systems having a membrane whose puncture zone may be facilely cleaned and disinfected. The invention comprises a housing having a first annular shoulder, and a duct extending longitudinally therethrough. Also included is a penetrable membrane having an outer surface with an annular indentation on the periphery thereof, and an inner surface that covers one end of the duct in the housing. The edge of the inner surface of the membrane abuts the first annular shoulder of the housing. A ring is disposed in the annular indentation in the outer surface of the membrane, and affixed to the housing. The outer surface of the ring is flush with the central portion of the outer surface of the membrane, which the ring circumscribes.

In a preferred embodiment of the invention, the outer circumference of the ring is affixed to the housing by an ultrasonic weld seam. Further, the housing also comprises a second annular shoulder, disposed so that the outer edge of the inner surface of the ring abuts the second shoulder.

In the manufacture of the present invention, the membrane is inserted into the housing, and subsequently locked by the ring's being fitted into the housing. As indicated above, a weld seam couples the outer circumference of the ring to the housing, which facilitates assembly. Such a weld is especially easy to produce, and seals the gap between the ring and the housing against the outside. Since, in assembling the invention, the membrane is not passed through the ring, the region where the ring covers the edge of the outer surface of the membrane may be chosen relatively large. While the edge of the membrane is held in this fashion so that the membrane tightly covers the duct in the housing, the membrane edge is not distorted by the ring. Any compression occurs exclusively in the direction of the longitudinal axis of the housing. Thus, the central outer surface of the membrane remains flat and smooth, flush with the outer surface of the ring. This permits satisfactory cleaning and disinfection of the puncture region of the membrane.

BRIEF DESCRIPTION OF THE DRAWING

The sole figure is a longitudinal section of a preferred embodiment of the invention, and a connecting piece.

DESCRIPTION OF THE PREFERRED EMBODIMENTS

The invention entails an injector for infusion or transfusion systems having a membrane whose puncture zone may be readily cleaned and disinfected.

Referring to the sole figure, a connecting piece 10 is inserted in a tube line which leads from a drip chamber to a patient. The connecting piece 10 is T-shaped, comprising a transfer duct 11 leading to the patient, and a nipple 12 containing a branch duct 13 opening into the transfer duct 11, and having an inner wall 14 widening conically to the outside. The nipple 12 is formed as a Luer female taper and has a locking member 15 on the outside.

An injector 16 comprises a male taper 17 which tightly fits into the female taper of the nipple 12. The male taper 17 is surrounded by a sleeve 18 having, on its inside, threads 19 for cooperating with the locking member 15 of the nipple 12. A duct 20, which extends longitudinally through a housing 16' of the injector 16, comprises an outer first section 21 having a first diameter, and an inner second section 22 having a second diameter smaller than the first. The sections 21 and 22 are separated by a porous material 23. The porous material 23 is pressed into a space formed by a section 24 of the housing 16'. The length of the diameter of the space formed by the section 24 is between that of the first and second diameters. Preferably, the porous material 23 is positioned against the walls of the section 24 exclusively by pressure. The housing 16' is preferably constructed in one piece of a thermoplastic plastic.

The section 21 of the duct 20 is bounded at its inner end by the porous material 23, and bounded at its outer end by a penetrable membrane 25. Preferably, the membrane 25 comprises latex. The membrane 25 is fixed in the outer end of the housing 16', having an edge 25a in contact with a cylindrical wall 26 of the housing 16'. An annular indentation 32 is disposed in the edge of the outer surface of the membrane 25. A ring 27 is disposed on the outside of the housing 16' flush with a flat outer face 25b of the membrane 25. The inner surface of the membrane 25 abuts a first annular shoulder 28 of the housing 16'. An annular bead 29 disposed on the first annular shoulder 28 buries itself into the inner surface of the membrane 25, for sealing purposes. The outer edge of the inner surface of the ring 27 preferably abuts a second annular shoulder 30 of the housing 16'. Preferably, the second annular shoulder 30 is bevelled downward inwardly, and the abutting surface of the ring 27 is correspondingly inclined. The plane tangent to the lower edge of the second annular shoulder 30 is parallel to the first annular shoulder 28. The ring 27 is affixed to the housing 16', preferably by an ultrasonic weld seam. Preferably, the seam comprises an ultrasonic weld seam 31 disposed between the outer circumference of the ring 27, and the housing 16'. The ring 27 fits into the annular indentation 32 in the membrane 25. The inside diameter of the ring 27 is preferably smaller than the diameter of the section 21.

The exterior of the housing 16' is cylindrical and preferably has a knurl 33, to facilitate gripping the housing 16', and screwing the housing 16' onto the nipple 12.

Preferably, the housing 16' comprises one piece of plastic, which can be manufactured separately, and need not undergo heat treatment after manufacture for the shaping or deformation of any separate parts. First, the porous material 23 is pressed into the housing 16'. Then, the section 21 of the duct 20 is covered with the membrane 25, and the ring 27 is inserted into the recess formed by the annular indentation 32 of the membrane 25 and the second annular shoulder 30 of the housing 16'. The membrane 25 is secured beneath the ring 27 by the production of the ultrasonic weld seam 31 between the ring 27 and the housing 16'. The outer surface of the ring 27 is flush with the outer face 25b of the membrane 25, and preferably flush with the exterior of the housing 16'. Any gaps between the ring 27 and the membrane 25 may be sealed with an adhesive.

While the invention has been described in its preferred embodiments, it is to be understood that the words which have been used are words of description rather than limitation and that changes may be made within the purview of the appended claims without departing from the true scope and spirit of the invention in its broader aspects.

We claim:

1. An injector for infusion and transfusion systems, comprising:
   a housing, having a first annular shoulder, an annular bead disposed on said first annular shoulder, and a duct extending longitudinally therethrough;
   a penetrable membrane, having an inner surface with and edge, and an outer surface, said outer surface having an annular indentation on the periphery thereof, and a flat central portion bordered by said annular indentation, said inner surface covering and end of said duct, and said edge abutting said first annular shoulder and said annular bead of said housing; and
   a ring, having an inner surface with an outer edge, and having an outer surface, disposed in said annular indentation of said membrane, and affixed to said housing, so that said outer surface of said ring is flush with said central portion of said outer surface of said membrane, which said ring circumscribes.

2. An injector as in claim 1 wherein said ring is affixed to said housing by an ultrasonic weld seam.

3. An injector as in claim 2 wherein said housing comprises a second annular shoulder disposed so that said outer edge of said inner surface of said ring abuts said second annular shoulder.

4. An injector as in claim 3 wherein said ultrasonic weld seam is disposed between said housing, and an outer circumference of said ring.

5. An injector as in claim 1 wherein said housing comprises a second annular shoulder, disposed so that said outer edge of said inner surface of said ring abuts said second annular shoulder.

6. An injector as in claim 5 wherein said ring is affixed to said housing by an ultrasonic weld seam disposed between said housing and an outer circumference of said ring.

* * * * *